(12) United States Patent
    Kim

(10) Patent No.: US 11,178,929 B2
(45) Date of Patent: Nov. 23, 2021

(54) EARMUFFS HAVING HOT PACKS THEREIN

(71) Applicant: Yeongmi Kim, Goyang-si (KR)

(72) Inventor: Yeongmi Kim, Goyang-si (KR)

( * ) Notice: Subject to any disclaimer, the term of this patent is extended or adjusted under 35 U.S.C. 154(b) by 155 days.

(21) Appl. No.: 16/626,627

(22) PCT Filed: Aug. 30, 2019

(86) PCT No.: PCT/KR2019/011154
    § 371 (c)(1),
    (2) Date: Dec. 26, 2019

(87) PCT Pub. No.: WO2020/085638
    PCT Pub. Date: Apr. 30, 2020

(65) Prior Publication Data
    US 2021/0330014 A1    Oct. 28, 2021

(30) Foreign Application Priority Data
    Oct. 23, 2018  (KR) .......................... 20-2018-0004813

(51) Int. Cl.
    *A42B 1/00*      (2021.01)
    *A42B 1/0188*    (2021.01)
    *A42B 1/008*     (2021.01)

(52) U.S. Cl.
    CPC ............ *A42B 1/0188* (2021.01); *A42B 1/008* (2013.01)

(58) Field of Classification Search
    CPC ............................... A42B 1/0188; A42B 1/008
    See application file for complete search history.

(56) References Cited

U.S. PATENT DOCUMENTS

| | | | | |
|---|---|---|---|---|
| 5,395,400 A | * | 3/1995 | Stafford | A42B 1/008 2/209 |
| 5,809,573 A | * | 9/1998 | Bary | A61F 7/03 128/866 |
| 2005/0065585 A1 | * | 3/2005 | Salas | A61F 7/03 607/109 |
| 2006/0100681 A1 | * | 5/2006 | Salas Carpizo | A61F 7/034 607/109 |
| 2009/0013447 A1 | * | 1/2009 | Drosihn | A42B 1/0188 2/209 |
| 2012/0324635 A1 | * | 12/2012 | Shapiro | A61F 9/029 2/423 |
| 2014/0304887 A1 | * | 10/2014 | Ilges | A42B 1/0186 2/172 |

(Continued)

FOREIGN PATENT DOCUMENTS

| | | |
|---|---|---|
| DE | 202017104346 U1 | 9/2017 |
| JP | 2018-086202 A | 6/2018 |

(Continued)

*Primary Examiner* — Khaled Annis
(74) *Attorney, Agent, or Firm* — KORUS Patent, LLC; Seong Il Jeong

(57) ABSTRACT

The present invention is directed to earmuffs, and is intended to allow for hot packs to be used, thereby improving the effect of protecting ear regions from cold and a cold wave in the winter season. In order to achieve this, the present invention provides earmuffs (10) including a pair of ear covers (11) and a band (12) configured to connect the ear covers (11), wherein reception slots (13) through which hot packs (20) configured to generate heat are inserted and stored are formed in the ear covers (11), respectively.

1 Claim, 9 Drawing Sheets

(56) References Cited

U.S. PATENT DOCUMENTS

| | | | |
|---|---|---|---|
| 2015/0157065 A1* | 6/2015 | Pierias | F24V 30/00 |
| | | | 126/204 |
| 2016/0058084 A1* | 3/2016 | Stevenson | A41D 20/005 |
| | | | 2/209.13 |
| 2019/0175391 A1* | 6/2019 | Shemtov | A61F 7/086 |
| 2020/0337892 A1* | 10/2020 | Timms | A61F 7/10 |

FOREIGN PATENT DOCUMENTS

| | | |
|---|---|---|
| KR | 20-0281389 Y1 | 7/2002 |
| KR | 10-2012-0048070 A | 5/2012 |
| KR | 20-2012-0003416 A | 5/2012 |
| KR | 10-1286036 B1 | 7/2013 |
| KR | 20-0481272 Y1 | 9/2016 |
| KR | 20-0489133 Y1 | 5/2019 |

* cited by examiner ns, and more
EARMUFFS HAVING HOT PACKS THEREIN

TECHNICAL FIELD

The present invention relates to earmuffs, and more specifically to earmuffs having hot packs therein, which allow for hot packs to be inserted and used in earmuffs that are intended to protect ear regions from cold in the winter season.

BACKGROUND ART

In general, many users use earmuffs for outdoor activities in the winter season. Such earmuffs are provided with a pair of cover members (ear covers) that are formed to allow ear regions to be comfortably positioned therein while entirely surrounding the ear regions.

Furthermore, the cover members are generally used in such a form that they are generally made of a material such as fur or wool to thus improve a warm-keeping property and they can be worn on the head by connecting both the cover members by a band-type elastic member.

However, the conventional earmuffs have a limitation to a warm-keeping function because they form covers configured to simply block the wind. Accordingly, heat generation-type earmuffs equipped with a heat generation function have recently been developed for users who use earmuffs in more extreme situations with severe cold.

However, most of such heat generation-type earmuffs generate heat using electricity as an energy source, and a rechargeable battery or battery is provided for this purpose. However, when a heat generation function is provided using a rechargeable battery or battery, a problem arises in that a period of use is shortened. When the capacity of the rechargeable battery or battery is increased to increase the period of use, a problem arises in that inconvenience increases due to weight during wearing.

DISCLOSURE

Technical Problem

The present invention has been conceived to overcome the above-described problems of the conventional art, and an object of the present invention is to develop earmuffs that can generate heat by using lightweight hot packs without requiring a separate power supply, thereby improving the usage comfort of the earmuffs.

Technical Solution

In order to accomplish the above object, the present invention provides earmuffs including a pair of ear covers and a band configured to connect the ear covers, wherein reception slots through which hot packs configured to generate heat are inserted and stored are formed in the ear covers, respectively.

Advantageous Effects

The earmuffs according to the present invention allow for the heat generation hot packs to be inserted and used in the ear covers, thereby providing the effect of improving the effect of protecting ear regions from cold and a cold wave in the winter season.

In particular, the hot packs are inserted and stored, thereby providing the advantage of preventing the risk of the loss of the hot packs during use.

MODE FOR INVENTION

Figure 1:
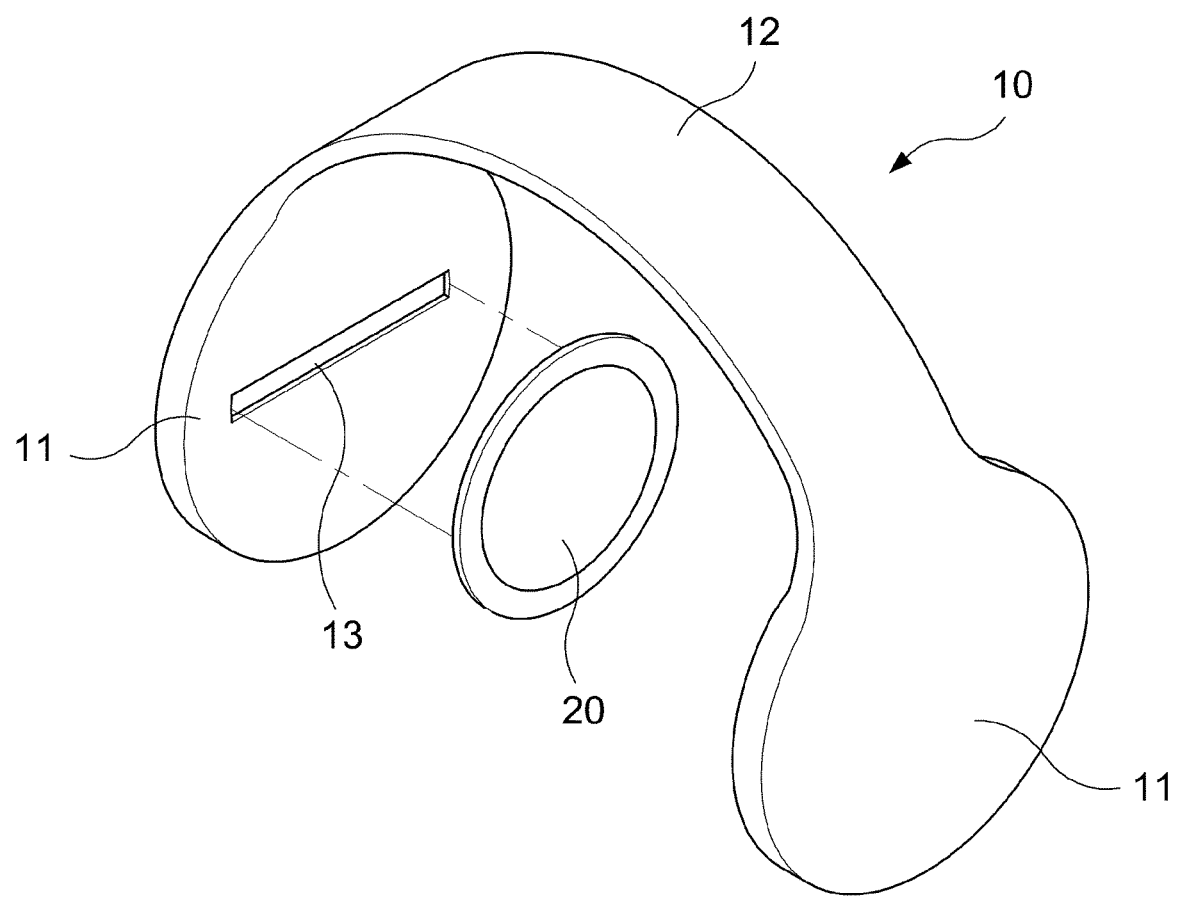
FIG. 1 is a perspective view of earmuffs according to a first embodiment of the present invention.
Figure 2:
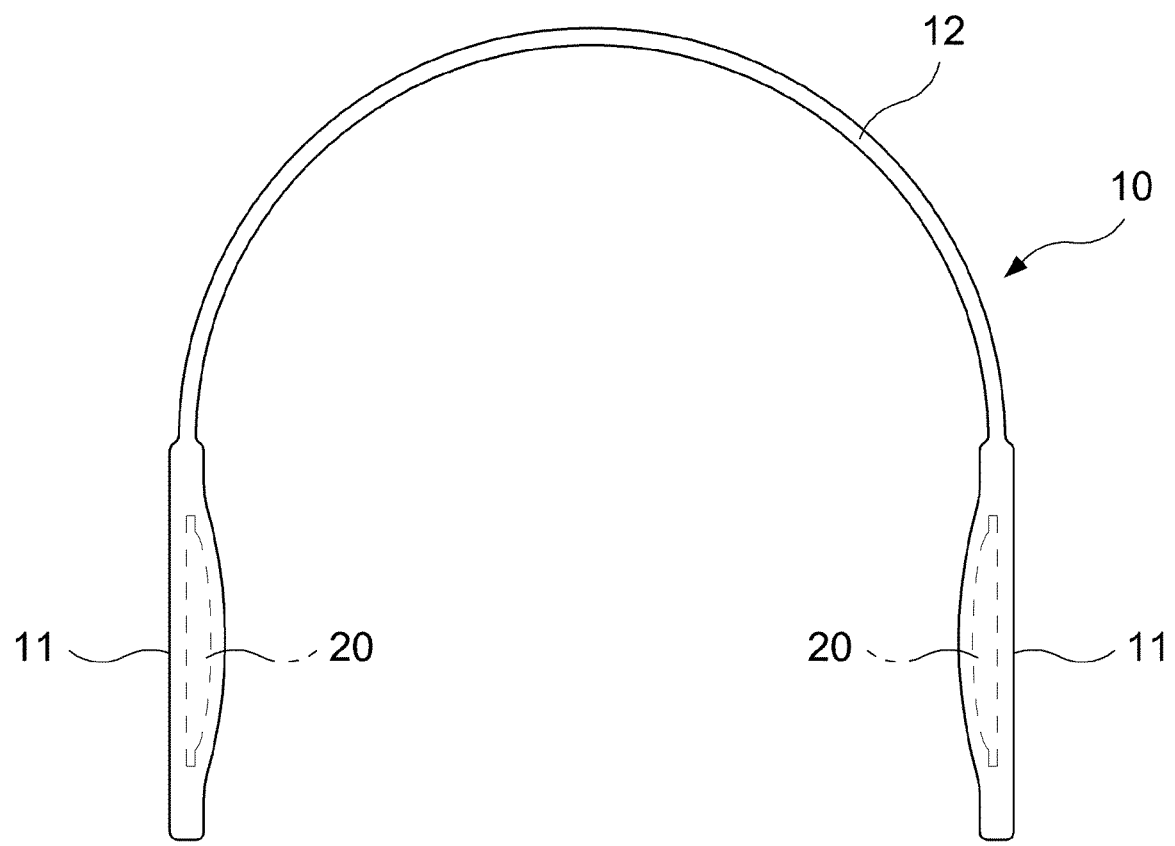
FIG. 2 is a view showing the structure of the front surface of the earmuffs according to the present invention.
Figure 3:
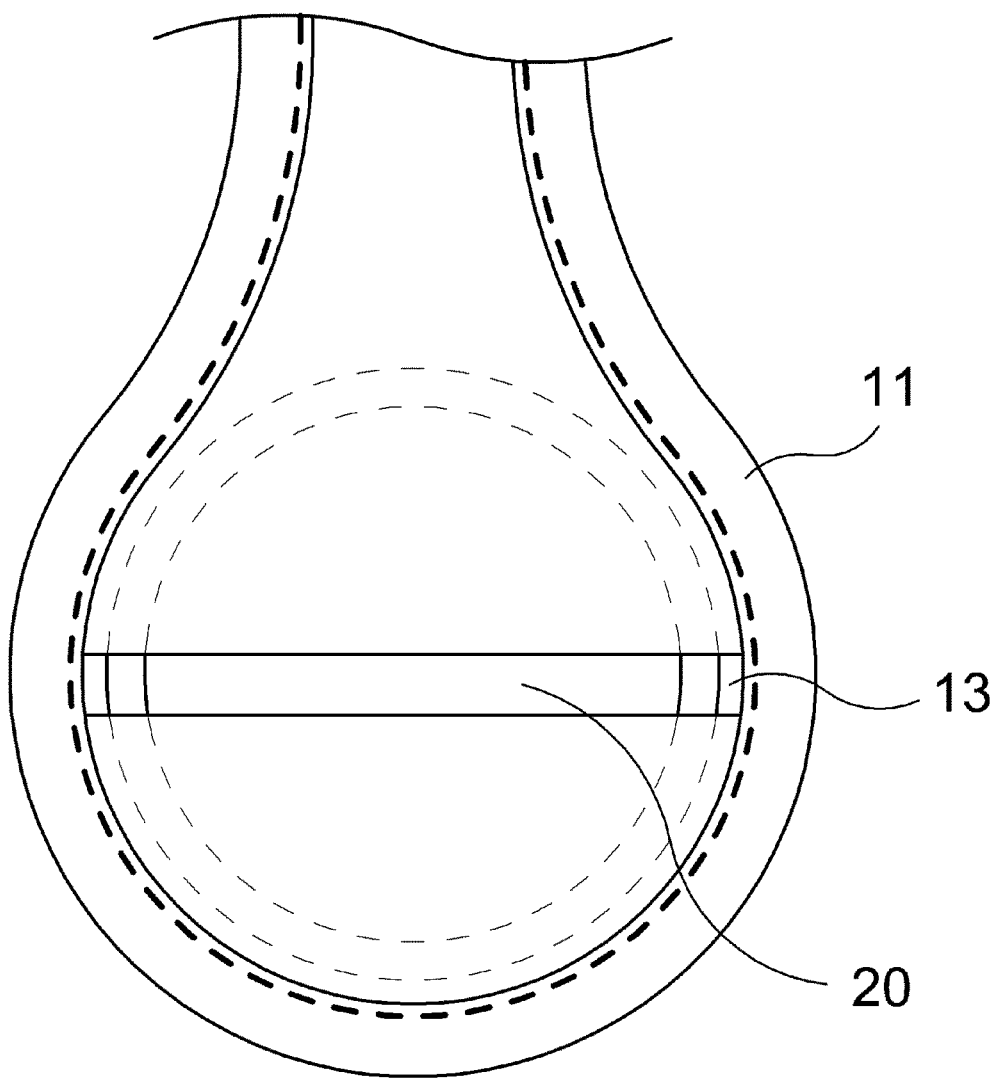
FIG. 3 is a detailed view showing a state in which hot packs have been inserted according to the present invention.
Figure 4:
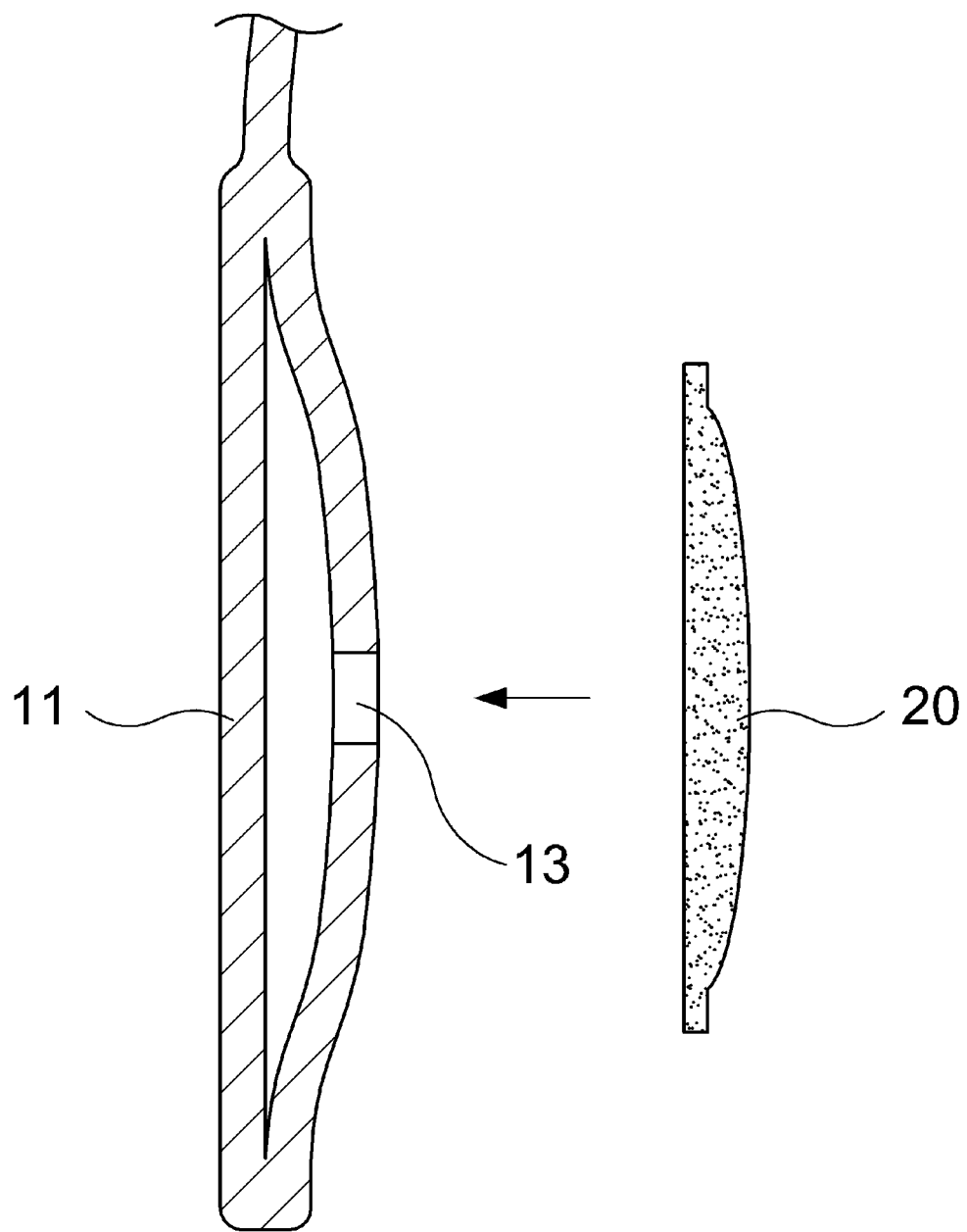
FIG. 4 is a sectional view showing the structure of a state in which the hot packs have been separated according to the present invention.
Figure 5:
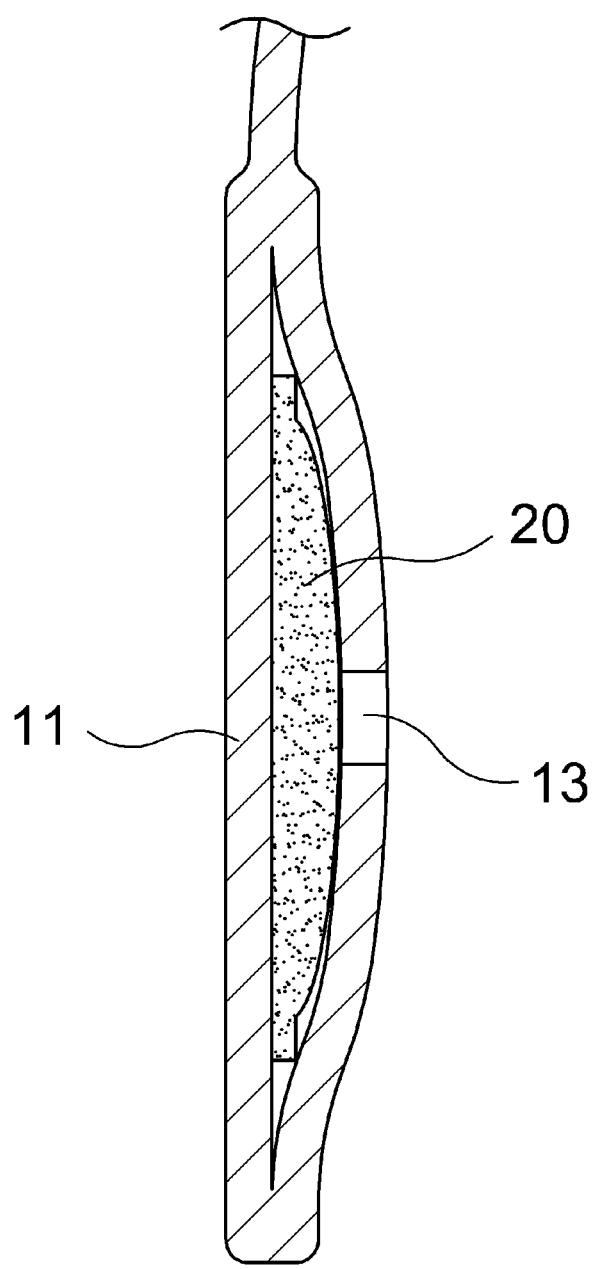
FIG. 5 is a sectional view showing the structure of the state in which the hot packs have been inserted according to the present invention.

Specific embodiments of the present invention will be described in detail below with reference to the accompanying drawings.

First, the structure of earmuffs according to a first embodiment of the present invention will be described with reference to FIGS. 1 to 5 below.

The earmuffs 10 according to the present embodiment include a pair of ear covers 11 and a band 12 configured to connect the ear covers 11 to each other.

In this case, it can be seen that the hot packs 20 configured to generate heat are inserted and provided in the ear covers 11.

For this purpose, reception slots 13 through which the hot packs 20 configured to generate heat may be inserted are formed in the ear covers 11 in lateral directions.

Operations and effects attributable to the use of the earmuffs according to the present invention, which are configured as described above, will be described below.

Figure 6:
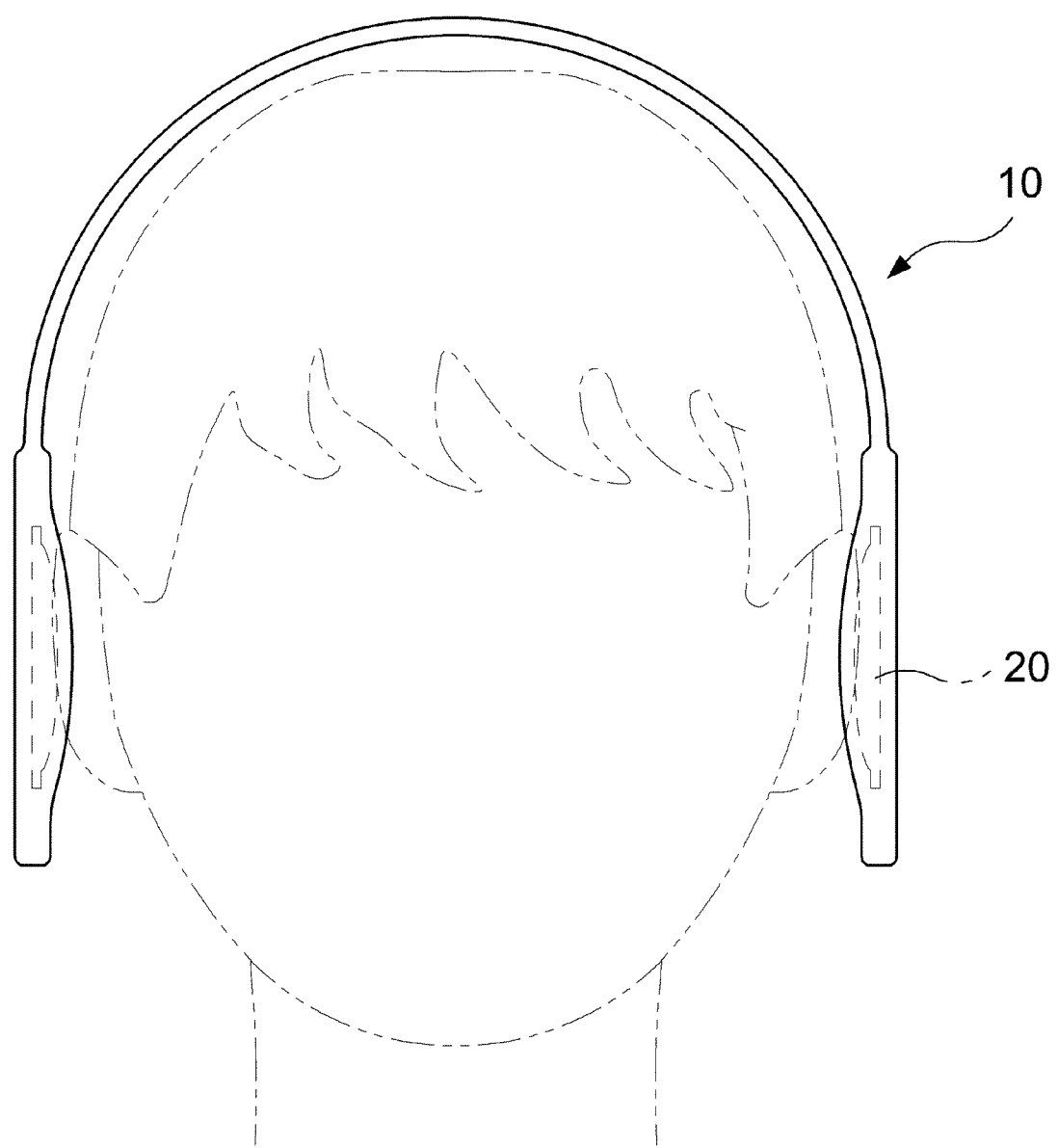
FIG. 6 is a view showing a state in which the earmuffs according to the present invention have been worn.

The earmuffs 10 according to the present invention are worn and used on the head part of a human, as shown in FIG. 6. In this case, the hot packs 20 are inserted into both the side ear covers 11 through the reception slots 13, and thus a continuous heat generation effect.

In other words, while the hot packs 20 are maintained in a stable storage state inside the ear covers 11 while being prevented from being exposed to the outside, the internal generation of heat is gradually performed, and thus heat is transferred to ear regions.

Accordingly, the earmuffs 10 according to the present invention perform self-heat generation via the hot packs 20 as well as a simple wind-blocking function, thereby providing the effect of maximizing a warm-keeping effect.

In particular, the lightweight hot packs 20 are used as a heat generation means, and thus an increase in weight attributable to a conventional electric heat generation means can be prevented, thereby providing the advantage of improving the wearing comfort of the earmuffs.

Furthermore, the hot packs 20 are stored in an internal insertion form that prevents the hot packs 20 from being exposed to the outside, thereby providing the advantage of preventing the hot packs from being lost in the process of using them.

Figure 7:
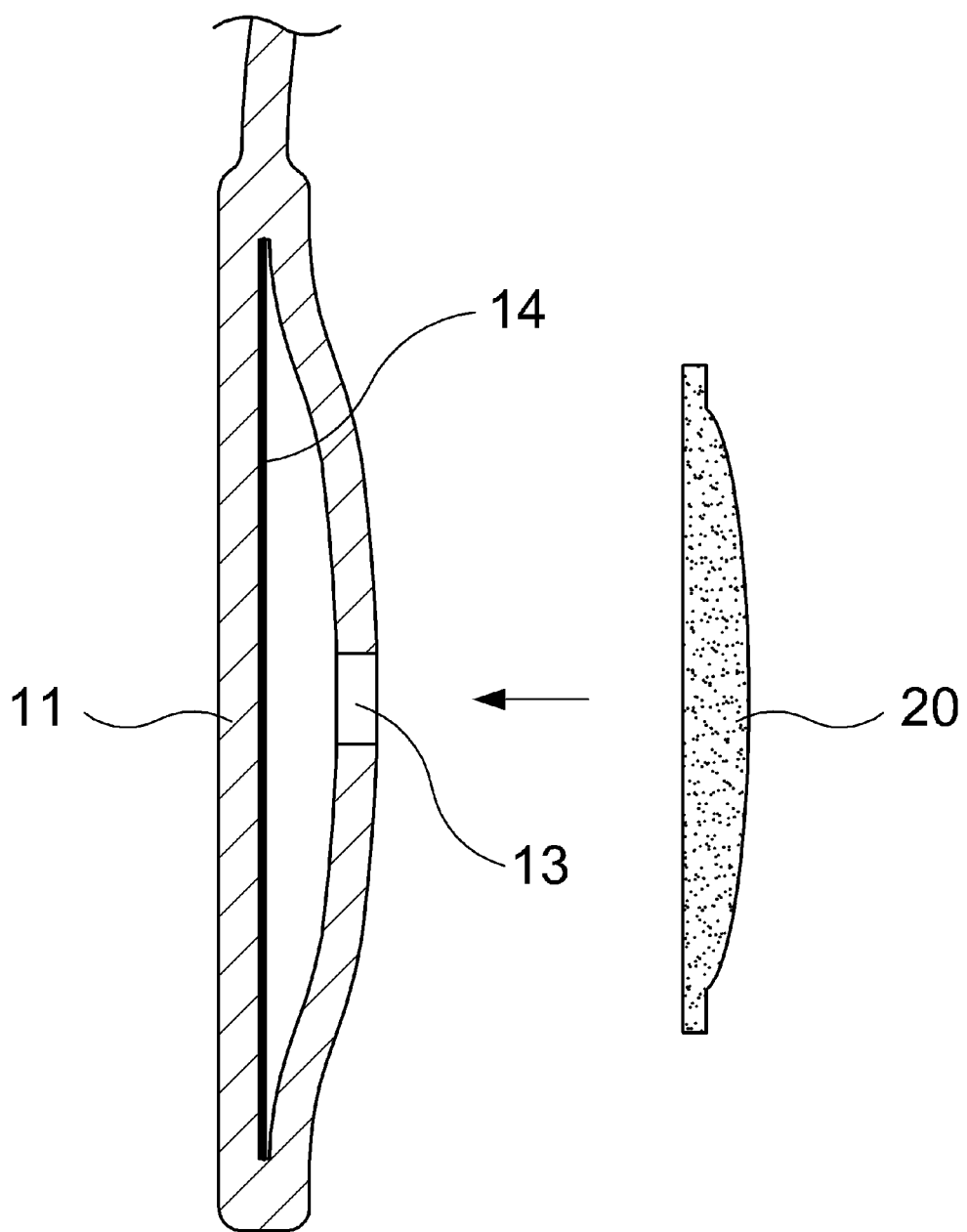
FIG. 7 is a sectional view showing the structure of each ear cover according to a second embodiment of the present invention.

Meanwhile, FIG. 7 is a view showing a configuration according to a second embodiment of the present invention, from which it can be seen that a heat reflection layer 14 configured to minimize thermal loss by reflecting the heat, generated in a corresponding one of the inserted hot packs 20, to the ear regions of a wearer is formed in the inner space of each of the reception slots 13.

In this case, the heat reflection layer 14 has a mixed composition of 20 to 40% by weight of Teflon, 20 to 40% by weight of aluminum, 10 to 30% by weight of glass fiber, 10 to 30% by weight of nano-silver, 1 to 10% by weight of ceramic resin, and 1 to 10% by weight of sodium hypochlorite.

When the earmuffs are configured as described above, the heat generated in the hot packs 20 is reflected inward without leaking to the outside, thereby preventing thermal loss and thus improving a warm-keeping effect.

In particular, Teflon mixed in the heat reflection layer 14 increases the density of the reflection layer to thus prevent cracking, aluminum and nano-silver improve heat reflection efficiency, and glass fiber improves the bonding force between materials such as aluminum and nano-silver.

Furthermore, sodium hypochlorite has the advantages of preventing discoloration and deformation caused by the oxidation of aluminum and nano-silver.

Figure 8:
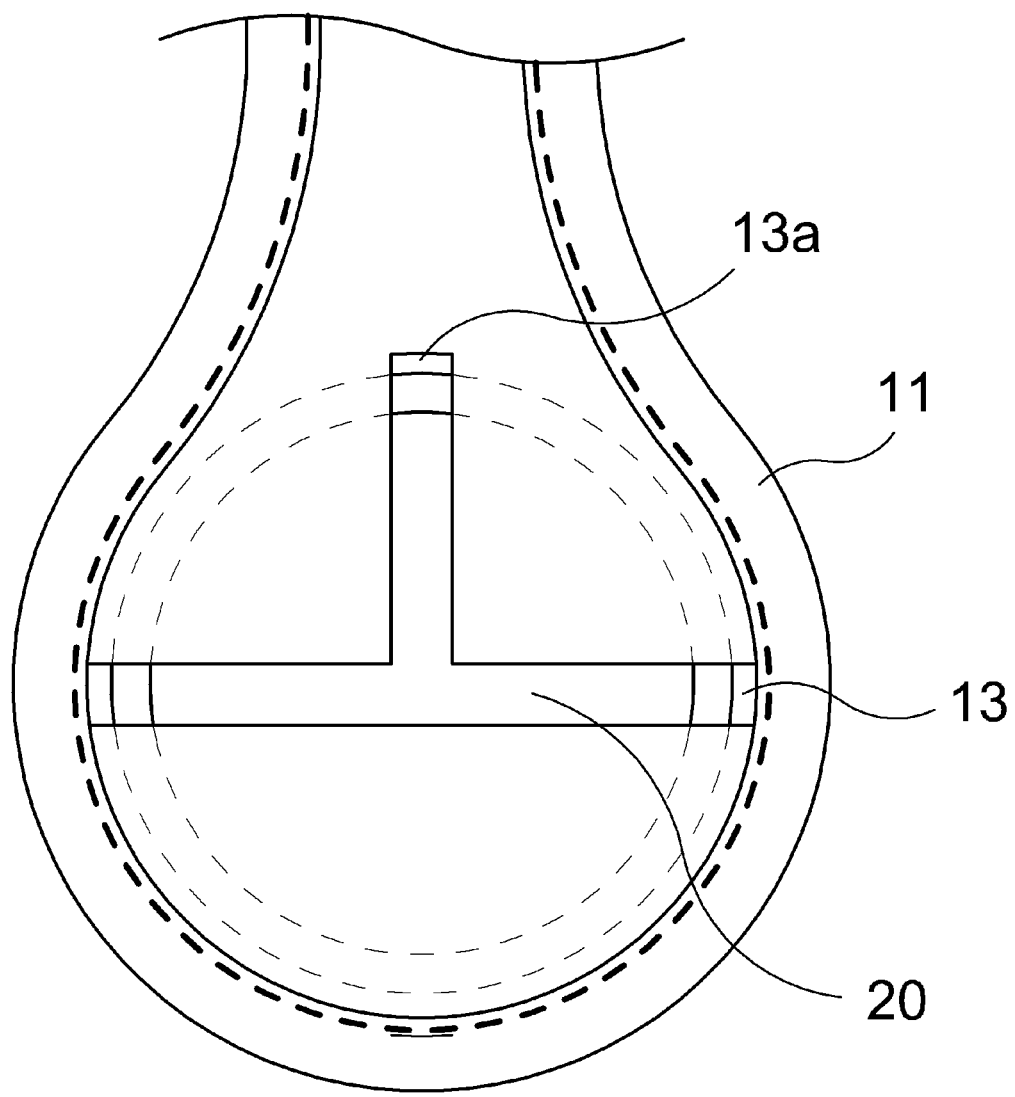
FIG. 8 is a view showing a state in which the reception slot of each ear cover according to a third embodiment of the present invention has been formed.

Furthermore, FIG. 8 is a view showing a configuration according to a third embodiment of the present invention, from which it can be seen that reception slots 13 are formed in lateral directions and an auxiliary slot 13a extends from the center of each of the reception slots 13 in a vertically upward direction.

When earmuffs are configured as described above, a "T"-shaped cutout structure is formed by the reception slot 13 and the auxiliary slot 13a, and thus the hot packs 20 may be easily inserted and replaced.

Figure 9:
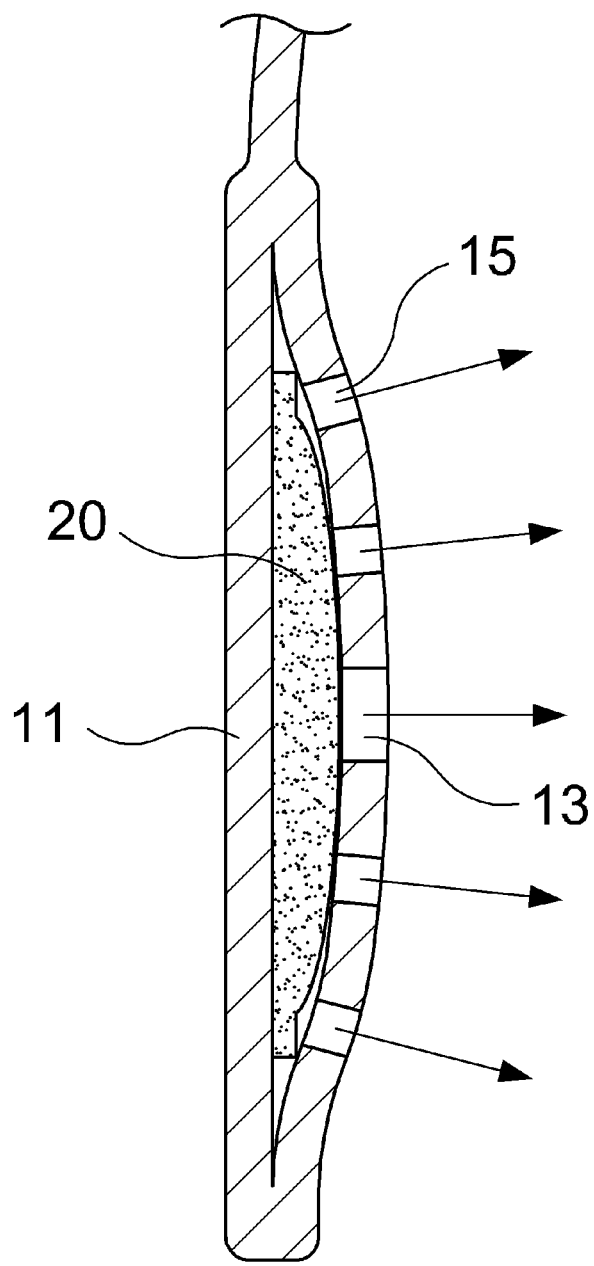
FIG. 9 is a sectional view showing the structure of the section of each ear cover according to a fourth embodiment of the present invention.

Furthermore, FIG. 9 is a view showing a configuration according to a fourth embodiment of the present invention, from which it can be seen that a plurality of through holes 15 is formed in each ear cover 11 so that the heat generated in hot packs 20 can be smoothly discharged.

When earmuffs are configured as described above, heat is more easily discharged, thereby providing the advantage of improving heat generation efficiency.

Furthermore, although the specific embodiments of the present invention have been described and illustrated, it will be apparent that the structure of the earmuffs according to the present invention may be modified and practiced in various forms by those skilled in the art.

Although the reception slots for the hot packs are described and illustrated as being formed in shapes that are formed in lateral directions in the embodiments as examples, the shapes and forms of the reception slots may be configured in vertical or diagonal directions as desired.

Therefore, such modified embodiments should not be individually understood from the technical spirit or scope of the present invention, but should be considered to be included within the appended claims of the present invention.

The invention claimed is:

1. Earmuffs (10) having hot packs therein, the earmuffs (10) comprising a pair of ear covers (11) and a band (12) configured to connect the ear covers (11), wherein reception slots (13), through which the hot packs (20) configured to generate heat are inserted, are formed in the ear covers (11), respectively;

wherein heat reflection layers (14) configured to minimize thermal loss by reflecting heat, generated in the hot packs (20), to ear regions of a wearer are formed inside the reception slots (13), respectively;

wherein the reception slots (13) are formed in lateral directions, and auxiliary slots (13a) extend from centers of the reception slots (13), respectively, in vertically upward directions;

wherein a plurality of through holes (15) is formed in the ear covers (11) so that heat generated in the hot packs (20) can be smoothly discharged; and wherein the heat reflection layers (14) have a mixed composition of 20 to 40% by weight of Teflon, 20 to 40% by weight of aluminum, 10 to 30% by weight of glass fiber, 10 to 30% by weight of nano-silver, 1 to 10% by weight of ceramic resin, and 1 to 10% by weight of sodium hypochlorite.

* * * * *